(12) United States Patent
Yarborough et al.

(10) Patent No.: US 12,064,735 B2
(45) Date of Patent: Aug. 20, 2024

(54) OSCILLATING BIOREACTOR SYSTEM

(71) Applicant: LIFECYCLE BIOTECHNOLOGIES, LP, Fort Worth, TX (US)

(72) Inventors: Cody Yarborough, Cleburne, TX (US); Ronald Gohdes, Granbury, TX (US)

(73) Assignee: Lifecycle Biotechnologies, LP, Cleburne, TX (US)

( * ) Notice: Subject to any disclaimer, the term of this patent is extended or adjusted under 35 U.S.C. 154(b) by 925 days.

(21) Appl. No.: 16/546,888

(22) Filed: Aug. 21, 2019

(65) Prior Publication Data
US 2020/0061556 A1 Feb. 27, 2020

Related U.S. Application Data

(60) Provisional application No. 62/720,396, filed on Aug. 21, 2018.

(51) Int. Cl.
| | |
|---|---|
| *B01F 29/00* | (2022.01) |
| *B01F 29/30* | (2022.01) |
| *B01F 29/81* | (2022.01) |
| *B01F 31/22* | (2022.01) |
| *B01F 35/00* | (2022.01) |

(Continued)

(52) U.S. Cl.
CPC ........ *B01F 29/40111* (2022.01); *B01F 29/30* (2022.01); *B01F 29/40221* (2022.01); *B01F 29/81* (2022.01); *B01F 31/22* (2022.01); *B01F 35/531* (2022.01); *B01F 35/55* (2022.01);
(Continued)

(58) Field of Classification Search
CPC .... B01F 29/40111; B01F 29/30; B01F 29/81; B01F 31/22; B01F 2101/44; B01F 29/4011; B01F 29/40221; B01F 35/531; B01F 29/40222; B01F 35/5311; B01F 35/5312; B01F 35/532; B01F 35/55; C12M 27/06; C12M 27/10; C12M 27/16; C12M 27/12; C12M 27/20
USPC ..... 366/213, 214, 200, 306, 307; 435/304.2; 220/669, 675
See application file for complete search history.

(56) References Cited

U.S. PATENT DOCUMENTS

| | | | | |
|---|---|---|---|---|
| 70,450 | A * | 11/1867 | McAvoy et al. | B65D 51/246 220/284 |
| 665,349 | A * | 1/1901 | Sewall | F17C 3/08 220/745 |

(Continued)

FOREIGN PATENT DOCUMENTS

| | | | | |
|---|---|---|---|---|
| DE | 2052103 | A * | 4/1972 | ............ C12M 23/08 |
| EP | 320348 | A * | 6/1989 | ............ C12M 23/08 |

(Continued)

OTHER PUBLICATIONS

International Search Report and Written Opinion received in International Application No. PCT/US2019/047430 mailed Oct. 29, 2019. (8 pages).

(Continued)

*Primary Examiner* — Charles Cooley
(74) *Attorney, Agent, or Firm* — Haynes and Boone, LLP

(57) ABSTRACT

A biological production system includes a mixing vessel and an agitation device. The mixing vessel includes an outer housing, an internal mixing structure, and a reaction chamber. The mixing vessel is configured to provide low shear agitation to materials in the reaction chamber in response to force from the agitation device.

24 Claims, 7 Drawing Sheets

(51) Int. Cl.
      *B01F 35/53*      (2022.01)
      *B01F 101/44*     (2022.01)
      *C12M 1/06*       (2006.01)
      *C12M 3/04*       (2006.01)
      *C12M 3/06*       (2006.01)

(52) U.S. Cl.
      CPC ............ *C12M 27/06* (2013.01); *C12M 27/10* (2013.01); *C12M 27/16* (2013.01); *B01F 2101/44* (2022.01)

(56) References Cited

U.S. PATENT DOCUMENTS

| | | | | |
|---|---|---|---|---|
| 1,103,366 A * | 7/1914 | Markens | ............... | A63F 9/0406 273/145 A |
| D101,984 S * | 11/1936 | Fuerst | ............................ | D9/565 |
| 3,341,184 A * | 9/1967 | Merrill | ................... | A47J 43/27 215/382 |
| 3,540,700 A * | 11/1970 | Whitton | ................... | A61M 5/14 435/298.2 |
| 3,542,344 A * | 11/1970 | Oberhauser | ........... | B01F 35/421 366/202 |
| 3,711,379 A * | 1/1973 | Adams | ................... | C12M 23/48 435/303.3 |
| 3,777,652 A * | 12/1973 | Engel | ..................... | A47J 43/042 99/275 |
| 3,893,887 A * | 7/1975 | Smith | ..................... | C12M 29/00 435/395 |
| 3,905,584 A * | 9/1975 | Ratowsky | ............ | G03D 13/046 396/633 |
| 3,944,124 A * | 3/1976 | Hexel | ..................... | B65D 1/265 220/675 |
| 3,946,903 A * | 3/1976 | Parker | .................. | B65D 1/0292 222/92 |
| 4,317,886 A * | 3/1982 | Johnson | ................. | C12M 25/06 435/299.2 |
| 4,330,216 A * | 5/1982 | Johnson | ................. | B01F 29/64 435/304.2 |
| D266,815 S * | 11/1982 | Durand | ........................ | D7/530 |
| 4,538,439 A * | 9/1985 | Frei | ........................ | B65D 7/46 220/672 |
| D291,656 S * | 9/1987 | Bussell | ........................ | D9/552 |
| 4,824,787 A * | 4/1989 | Serkes | .................. | C12M 23/26 220/675 |
| 4,829,004 A * | 5/1989 | Varani | .................. | C12M 27/22 435/304.2 |
| 4,912,058 A * | 3/1990 | Mussi | .................. | C12M 25/06 366/233 |
| 4,962,033 A * | 10/1990 | Serkes | .................. | C12M 23/08 435/395 |
| 5,010,013 A * | 4/1991 | Serkes | .................. | C12M 27/20 220/672 |
| 5,084,393 A * | 1/1992 | Rogalsky | ............... | C12M 23/02 215/386 |
| D329,170 S * | 9/1992 | Hoffer | ........................... | D7/529 |
| 5,272,084 A * | 12/1993 | O'Connell | ............ | C12M 25/06 435/395 |
| 5,299,864 A * | 4/1994 | Reynolds | ............... | B01F 29/31 366/233 |
| D365,248 S * | 12/1995 | Falzarano | ..................... | D7/529 |
| 5,499,872 A * | 3/1996 | Baxter | ................... | B01F 31/22 366/208 |
| 5,582,957 A * | 12/1996 | Sirianni | ................. | G03C 1/025 220/604 |
| 5,704,504 A * | 1/1998 | Bueno | ................. | B65D 79/0084 215/381 |
| 5,800,058 A * | 9/1998 | Cook | ..................... | B01F 35/55 366/307 |
| 5,866,419 A * | 2/1999 | Meder | .................. | C12M 27/12 435/298.2 |
| 5,908,127 A * | 6/1999 | Weick | .................. | B65D 1/0223 215/373 |
| 5,988,417 A * | 11/1999 | Cheng | .................. | B65D 1/0223 220/675 |
| 6,150,159 A * | 11/2000 | Fry | ......................... | C12M 23/08 435/298.2 |
| 6,190,913 B1 | 2/2001 | Singh | | |
| 6,837,610 B2 * | 1/2005 | Cadogan | ................ | B01F 35/55 366/144 |
| 6,857,531 B2 * | 2/2005 | Slat | .................... | B65D 79/0081 215/381 |
| 7,228,981 B2 * | 6/2007 | Chisholm | ............ | B65D 1/0223 220/675 |
| 7,247,471 B2 * | 7/2007 | Kadar | .................... | C12M 23/02 215/382 |
| 7,449,331 B2 * | 11/2008 | Whitley | ................. | C12M 23/02 220/675 |
| 7,469,796 B2 * | 12/2008 | Kamineni | ............ | B65D 1/0223 220/675 |
| 7,604,140 B2 * | 10/2009 | Pritchett, Jr. | ....... | B65D 79/0084 215/381 |
| 7,832,582 B2 * | 11/2010 | Roubal | ................ | B65D 1/0223 220/675 |
| 7,882,971 B2 * | 2/2011 | Kelley | ................. | B65D 1/0223 215/381 |
| 8,091,720 B2 * | 1/2012 | Colloud | ............... | B65D 1/0223 220/675 |
| 8,113,368 B2 * | 2/2012 | Oguchi | ................ | B65D 1/0223 215/381 |
| 8,113,370 B2 * | 2/2012 | Zhang | ..................... | B65D 1/40 215/381 |
| 8,186,528 B2 * | 5/2012 | Melrose | ............. | B65D 79/0084 215/381 |
| 8,276,775 B2 * | 10/2012 | Boukobza | .......... | B65D 79/0084 215/381 |
| 8,439,214 B2 * | 5/2013 | Darr | ..................... | B65D 1/0223 220/675 |
| 8,556,098 B2 * | 10/2013 | Peykoff | .................... | B65D 1/44 215/381 |
| 8,561,822 B2 * | 10/2013 | Beck | ........................ | B65D 1/44 220/672 |
| 8,567,622 B2 * | 10/2013 | Yourist | ................ | B65D 1/0253 220/666 |
| 8,567,623 B2 * | 10/2013 | Shah | .................... | B65D 79/0084 220/666 |
| 8,616,395 B2 * | 12/2013 | Patcheak | ............... | B65D 1/0276 215/381 |
| 8,623,640 B2 | 1/2014 | Kunas et al. | | |
| 8,640,900 B2 * | 2/2014 | Heisner | ................ | B65D 23/102 220/675 |
| D701,427 S * | 3/2014 | Edmund | ..................... | D7/624.2 |
| 8,668,100 B2 * | 3/2014 | Castillo Higareda | ....................... | B65D 1/0223 220/660 |
| 8,714,385 B2 * | 5/2014 | Jung | .................. | B65D 1/023 220/666 |
| 8,881,922 B2 * | 11/2014 | Schlies | ............... | B65D 79/0084 215/381 |
| 8,945,917 B2 | 2/2015 | Sarkar et al. | | |
| 8,951,785 B2 | 2/2015 | Fatherazi et al. | | |
| 9,187,211 B2 * | 11/2015 | Kappes | ............... | B02C 17/1825 |
| D756,233 S * | 5/2016 | Romero Salido | ............. | D9/542 |
| 10,787,287 B2 * | 9/2020 | Usami | ................. | B65D 1/0223 |
| 11,390,417 B2 * | 7/2022 | Usami | ................. | B65D 79/0084 |
| 11,661,229 B2 * | 5/2023 | Yourist | ................... | B65D 85/72 220/675 |
| 2002/0155594 A1* | 10/2002 | Hsieh | ..................... | C12M 25/14 435/395 |
| 2003/0015491 A1* | 1/2003 | Melrose | ................. | B65D 79/0084 215/381 |
| 2003/0231546 A1 | 12/2003 | Bibbo et al. | | |
| 2004/0211747 A1* | 10/2004 | Whitley | ................. | C12M 23/08 220/666 |
| 2004/0233777 A1* | 11/2004 | Adams | .................... | B44D 3/08 366/339 |
| 2005/0101009 A1* | 5/2005 | Wilson | ................. | C12M 23/08 435/295.3 |

(56) References Cited

U.S. PATENT DOCUMENTS

| | | | |
|---|---|---|---|
| 2006/0283832 A1* | 12/2006 | De Cleir | B65D 1/44 220/675 |
| 2007/0224676 A1* | 9/2007 | Haq | C12M 41/44 435/298.2 |
| 2008/0206734 A1* | 8/2008 | Asgari | C12M 27/20 435/383 |
| 2008/0206735 A1* | 8/2008 | Asgari | C12M 23/08 435/395 |
| 2009/0212053 A1* | 8/2009 | Lardino | A47G 19/2205 220/62.12 |
| 2011/0212519 A1* | 9/2011 | Wilson | C12M 23/24 435/325 |
| 2011/0281343 A1 | 11/2011 | Gay | |
| 2013/0153531 A1* | 6/2013 | Schlies | B65D 1/0223 215/381 |
| 2013/0306660 A1* | 11/2013 | Bysick | B65D 1/0223 220/669 |
| 2013/0313258 A1* | 11/2013 | Sines | B65D 83/0083 220/780 |
| 2014/0001190 A1* | 1/2014 | Deyerl | B65B 3/022 220/675 |
| 2014/0183202 A1* | 7/2014 | Hanan | B65D 1/44 220/669 |
| 2015/0037225 A1* | 2/2015 | Cordisco | B01F 31/10 134/135 |
| 2016/0040113 A1 | 2/2016 | Der et al. | |
| 2016/0270598 A1* | 9/2016 | Vu | A47J 43/0777 |
| 2017/0368518 A1* | 12/2017 | Drake | B65D 1/0223 |
| 2020/0061556 A1* | 2/2020 | Yarborough | B01F 35/531 |

FOREIGN PATENT DOCUMENTS

| | | | | |
|---|---|---|---|---|
| EP | 345415 A | * | 12/1989 | B65D 1/0223 |
| EP | 700990 A2 | * | 3/1996 | C12M 23/34 |
| EP | 761811 A2 | * | 3/1997 | |
| EP | 1245670 A2 | * | 10/2002 | C12M 23/08 |
| EP | 1400584 A2 | * | 3/2004 | B65D 21/0231 |
| EP | 1400585 A1 | * | 3/2004 | C12M 23/02 |
| FR | 1004626 | * | 4/1952 | |
| GB | 2062481 A | * | 5/1981 | B01F 11/0002 |
| GB | 2334965 A | * | 9/1999 | C12M 23/08 |
| JP | 06022745 A | * | 2/1994 | C12M 23/06 |
| WO | 97/08291 A1 | * | 3/1997 | |
| WO | WO 2008/098165 A2 | | 8/2008 | |
| WO | WO 2014/141136 A1 | | 9/2014 | |
| WO | WO-2015160614 A1 | * | 10/2015 | B01F 15/00876 |
| WO | WO 2017/127393 A1 | | 7/2017 | |

OTHER PUBLICATIONS

International Preliminary Report on Patentability received in International Application No. PCT/US2019/047430 issued Feb. 23, 2021. (7 pages).

* cited by examiner

OSCILLATING BIOREACTOR SYSTEM

FIELD OF INVENTION

This disclosure relates in general to chemical reactors and more particularly to an oscillating bioreactor system.

BACKGROUND

Mixing vessels used for media production or cellular growth production, collectively called bioreactors, are available to the marketplace in many forms.

The simplest bioreactors are rigid open-head vessels that employ a secondary mixing impeller inserted into the vessel to provide agitation. Nevertheless, bioreactors with secondary mixing devices raise concerns for sensitive biological production. First, the mixing vessel must be opened in order to introduce the mixing device, risking environmental contamination of the fluid inside the vessel. Additionally, the size of the impellor blades is limited by the size of the vessel's opening. Generally, impellor blades are sized relative to the container volume, the viscosity of the liquid contained therein, and desired processing environment, however, bioreactors tend to have an opening much smaller than the body of the mixing vessel. Accordingly, to fit within the vessel opening, the impellor blade(s) in many bioreactor systems are undersized and must be used at a high rotational speed to achieve sufficient mixing. The high rotational speed creates a high-shear environment at the fluid/blade interface, which is disfavored for biological production because large shear forces can disrupt the cells of interest or the proteins needed to support cell growth.

To address these issues, some bioreactors include an internal agitation system and/or an anti-contamination system to minimize the introduction of contaminants to the mixing vessel; however these bioreactor systems are complex and expensive. Prolonged storage within these vessels decreases their productivity, thus to reduce equipment costs, bioreactors with an internal agitation system and/or an anti-contamination system are often employed only as processing vessels, which means that the reaction mixture must be transferred to a secondary storage container post-processing. Transferring the reaction mixture not only increases production costs but adds processing risks such as microbial contamination, cell inhibition, worker exposure and loss of a stable harmonious environment.

A third type of bioreactor employs a fluid filled plastic bag as a processing chamber. In such systems, agitation is applied externally by tilting, rotating or mechanical pressure. While these bag-type bioreactors provide sterile, low shear agitation, they lack the ability to internally mix components such as media ingredients because the fluid within the bioreactor is moving at approximately the same speed. Additionally, these bag-type bioreactors are expensive, cumbersome and require transferring the fluid to an additional storage container post-processing, thus introducing another point of possible contamination.

Thus, there is a need for an inexpensive bioreactor which provides sterile, low shear agitation. There is also a need for an inexpensive bioreactor that is able to act as a storage container, post-processing.

BRIEF DESCRIPTION OF THE DRAWINGS

For a more complete understanding of the present disclosure and its advantages, reference is now made to the following description, taken in conjunction with the accompanying drawings, in which.

DETAILED DESCRIPTION OF THE DISCLOSURE

Figure 1A:
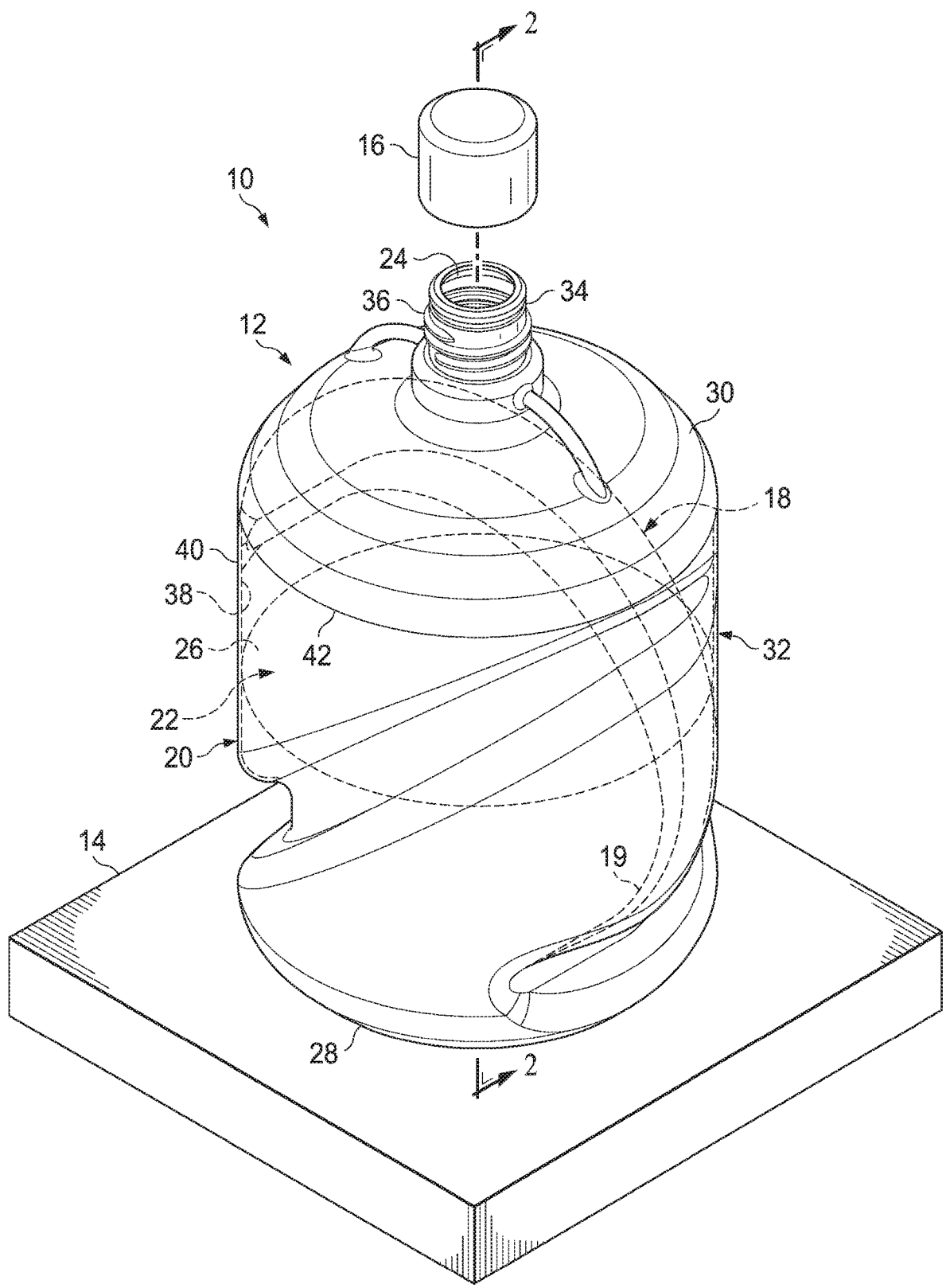
FIG. 1A illustrates an example biological production system, according to one or more embodiments.

In the various embodiments, the same reference numeral may be used in more than one figure. This reuse of a reference numeral in different figures represents the same element in the different figures.

Figure 1B:
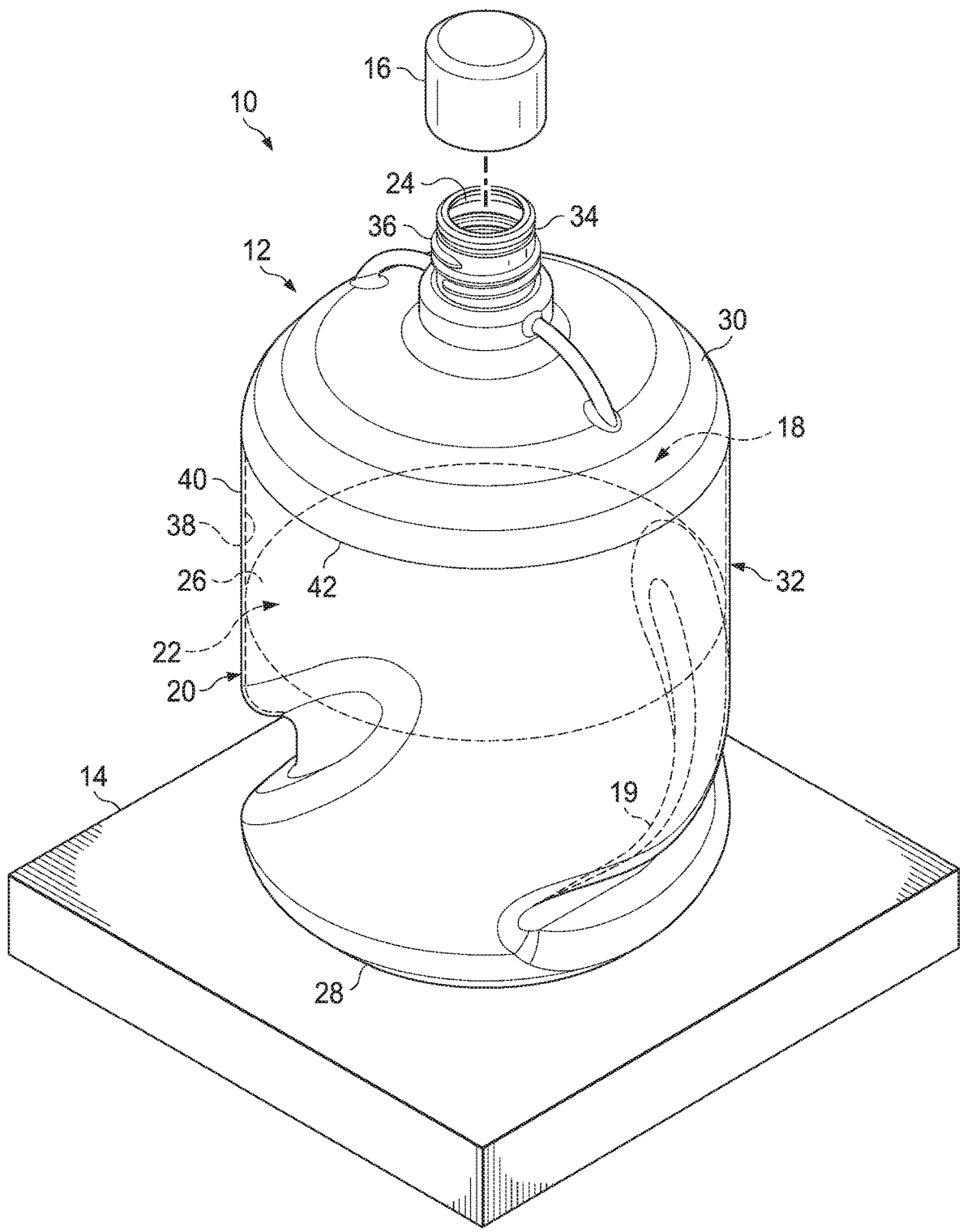
FIG. 1B illustrates an example biological production system, according to one or more embodiments.

FIGS. 1A and 1B illustrate system 10 for biological production in which system 10 includes mixing vessel 12 and agitation device 14. In one or more embodiments, system 10 optionally includes closure 16.

Mixing vessel 12 is a rigid, fixed-volume container operable for use as a bioreactor when sealed with a closure 16. Mixing vessel 12 includes internal mixing structure 18, outer housing 20, reaction chamber 22, and opening 24. Internal mixing structure 18 extends from, and is continuous with, outer housing 20 and together they define reaction chamber 22. In use, a fluid 26 is disposed in the reaction chamber 22.

Internal mixing structure 18 is an interior structure that extends from and is fabricated concurrently with outer housing 20 from a single unitary material. Internal mixing structure 18 includes at least one smooth three-dimensional mixing curve that completely or partially traverses the circumference of reaction chamber 22 as it travels from bottom end 28 toward top end 30 or from top end 30 toward bottom end 28. As shown in FIG. 1A, in one or more embodiments, internal mixing structure 18 is a continuous double helix-like structure that extends from bottom end 28 to top end 30.

In one or more embodiments, internal mixing structure 18 includes a mixing curve that traverses less than entire the circumference of reaction chamber 22. For example, internal mixing structure 18 may include a mixing curve that traverses 30 degrees, 60 degrees, 90 degrees, 180 degrees, or 270 degrees along the circumference of reaction chamber 22. In one or more embodiments, internal mixing structure 18 includes a mixing curve that traverses the entire circumference of reaction chamber 22. In one or more embodiments, internal mixing structure 18 includes a mixing curve that traverses the entire circumference of reaction chamber 22 more than once. For example, internal mixing structure 18 may include a mixing curve that traverse 360 degrees, 540 degrees, or 720 degrees along the circumference of reaction chamber 22. In one or more embodiments, internal mixing structure 18 includes multiple smooth three-dimensional mixing curves that traverse the entire circumference of reaction chamber 22 one or more times as they travel from bottom end 28 to top end 30. In one or more embodiments, internal mixing structure 18 may include a three-dimensional mixing curve that traverses the circumference of reaction chamber 22 more than once. In one or more embodiments, internal mixing structure 18 may include one or more mixing curves that include multiple pitches.

In one or more embodiments, internal mixing structure 18 may include a mixing curve having a height that is 10-100%, 20-90%, 30-80%, 40-70%, or 50-60% the height of mixing vessel 12. For example, a mixing curve may start near top end 30 and only travel to the midpoint of reaction chamber 22 or mixing vessel 12. As another example, and as shown in FIG. 1B, the mixing curve of internal mixing structure 18 begins near bottom end 28 and only travels to the approximate midpoint of reaction chamber 22. As used herein, mixing curves and other structures (e.g., internal mixing structure 18) are said to begin "near" bottom end 28 if they begin a distance of less than 5% of the total height of cylindrical wall 32 from bottom end 28. In the exemplary embodiment shown in FIG. 1B, internal mixing structure 18 runs from about 40% to about 50% of the height of cylindrical wall 32. In this exemplary embodiment, fluid 26 includes a less disturbed layer near the surface and a well-mixed layer below the surface. Non-uniform mixing may be beneficial in certain cell growth environments and/or may allow for certain components (e.g., reaction by-products) to be decanted if necessary.

Returning now to FIG. 1A, with continued reference to FIG. 1B, internal mixing structure 18 has one or more raised surfaces 19 that extend into reaction chamber 22 and create fluid movement within reaction chamber 22 when a rotational force is applied to mixing vessel 12. In one or more embodiments, the edges of internal mixing structure 18 and/or raised surfaces 19 are smooth and include no sharp edges, connecting instead in a rounded edge or chamfered corner. In one or more embodiments, raised surfaces 19 and internal mixing structure 18 include no edges and instead form a rounded surface with a radius of at least 0.5 inches. In some embodiments, the raised surfaces 19 and internal mixing structure 18 may have an average radius, based on the volume of mixing vessel 12, of 0.25-2 mm/L, 0.5-1.75 mm/L, 0.75-1.5 mm/L, or 1-1.25 mm/L. In one or more embodiments, an average depth of raised surfaces 19 measured from cylindrical wall 32, based on the volume of mixing vessel 12, may be 0.25-2 mm/L, 0.5-1.75 mm/L, 0.75-1.5 mm/L, or 1-1.25 mm/L.

The surface area of raised surfaces 19 will vary with the size of the container and the desired mixing parameters. In one or more embodiments, raised surfaces 19 have a surface area of from about 0% to 70%, 10-70%, 20-60%, 30-50%, or 30-40% of the surface area of cylindrical wall 32. Raised surfaces 19 are sized and shaped to enable the mixing of fluid 26 while maintaining a low shear environment within reaction chamber 22. In one or more embodiments, internal mixing structure 18 and/or raised surfaces 19, allow low shear mixing of fluid 26 within reaction chamber 22 when a rotational force is applied to mixing vessel 12.

Although low shear mixing can have many meanings in different contexts, generally low shear mixing is characterized as blending the components of a heterogeneous system without reducing the particle size or damaging the system components. When discussing low shear mixing for systems for biological production (e.g., system 10), low shear mixing takes on a particularized meaning when the system is being used for processes that involve the mixing of cells. In these applications, the term "low shear mixing" implies that the cells are blended in a manner than causes little or no lysis, i.e., the disintegration of the cell due to the rupture of the cell's walls or membranes. As used herein, when a system is used for the production of cells, an environment (e.g., the inside of a bio-reactor and/or reaction chamber 22) is "low shear" when the shear forces within the environment are sufficiently low (relative to the system components being mixed) such that the forces within the environment do not cause the component cells to lyse. For example, when handling blood cells, a low shear environment has a shear rate from about $0.5\ s^{-1}$ to about $20\ s^{-1}$.

Figure 3:
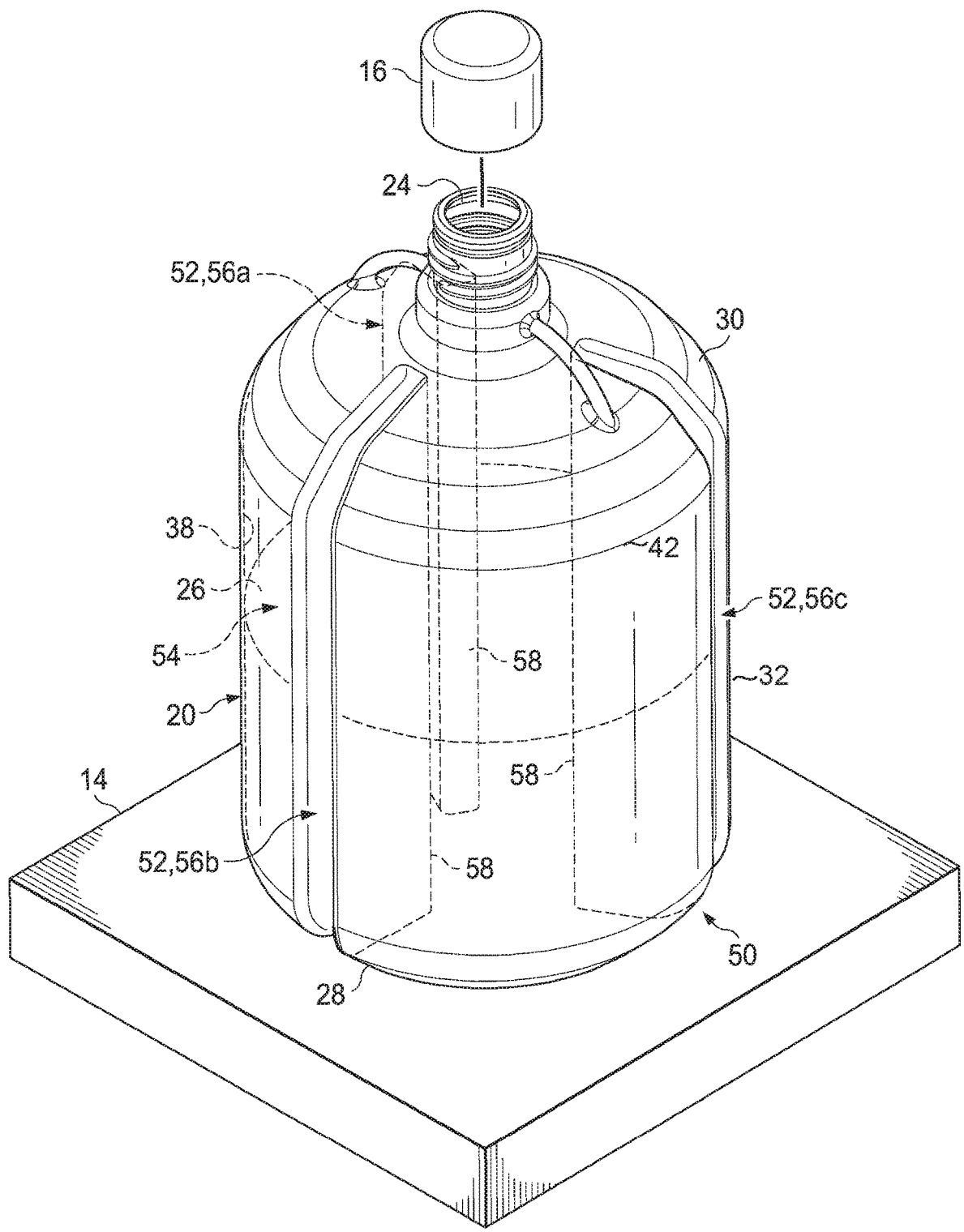
FIG. 3 illustrates an alternate embodiment of a mixing vessel of the biological system of FIG. 1.

In one or more embodiments, reaction chamber 22 has a low shear environment with a shear rate from about $0.01\ s^{-1}$ to about $500\ s^{-1}$, from about $0.1\ s^{-1}$ to about $100\ s^{-1}$, or from about $0.5\ s^{-1}$ to about $20\ s^{-1}$. In one or more embodiments, reaction chamber 22 is a low shear environment with a shear rate from about $0.5\ s^{-1}$ to about $20\ s^{-1}$ and outer housing 20 is a continuous, rigid shell that forms the outer confines of mixing vessel 12. Outer housing 20 extends from closed bottom end 28 along cylindrical wall 32 to an opposing top end 30 and concludes at opening 24. In one or more embodiments, top end 30 tapers from cylindrical wall 32 to neck portion 34. In one or more embodiments, top end 30 may be flat or substantially flat. In one or more embodiments, neck portion 34 may include interior or exterior threads 36, as shown in FIGS. 1A, 1B and 3.

Outer housing 20 has an interior facing side 38 and an exterior facing side 40. In one or more embodiments, outer housing 20 retains a generally uniform thickness. In one or more embodiments, outer housing 20 has a thickness that is proportional to the volume of mixing vessel 12. For example, the outer housing 20 may have a thickness of 0.01-0.30 mm/L, 0.05-0.25 mm/L, 0.08-0.20 mm/L, or 0.12-0.16 mm/L, based on the volume of the mixing vessel 12. In one or more embodiments and as seen in FIGS. 1A and 1B, the exterior facing side 40 of outer housing 20 retains a generally cylindrical shape. However, internal mixing structure 18 extends from outer housing 20 and outer housing 20 generally follows the contours of internal mixing structure 18. Accordingly, whereas outer housing 20 retains a substantially cylindrical exterior facing side 40, interior facing side 38 is generally non-cylindrical due to the one or more raised surfaces 19 which cause the shape of the interior facing side 38 of outer housing 20 to depart from a substantially cylindrical profile.

Outer housing 20 may be constructed from any material or combination of materials that are compatible with the expected product mixture and processing requirements. In one or more embodiments, outer housing 20 is constructed from tantalum, glass, stainless steel, aluminum, polymer compositions and combinations thereof. In one or more embodiments, outer housing 20 is constructed from a material suitable for aseptic processing. For example, outer housing 20 may be made of metal such as stainless steel or certain plastics and/or polymer compositions. In one or more embodiments, outer housing 20 is formed from a thermoplastic material such as polypropylene, polyethylene, polycarbonate and other polymers. In one or more embodiments, outer housing 20 may be formed from materials that enable mixing vessel 12 to be sterilized by conventional means such as steam, gamma irradiation, chemical or e-beam radiation.

Outer housing 20 may be molded, cast, or fabricated to minimize cost. While outer housing 20 is a continuous, uniform body formed from a single unitary material, as seen in FIGS. 1A and 1B, in one or more embodiments, outer housing 20 includes one or more seams, areas of overlap, connection points, non-uniformities, or other byproducts of the manufacturing process. For example, cylindrical wall 32 may include one or more connection points, such as top edge 42. As another example, there may be a bottom edge (not shown) where bottom end 28 connects to cylindrical wall 32 or a top edge 42 where cylindrical wall 32 connects to top end 30. However, in one or more embodiments, outer housing 20 may be seamless or substantially seamless. Additionally, in one or more embodiments, bottom end 28, cylindrical wall 32, and outer housing 20 may comprise one or more notches, indentations, dimples, trenches, or internal structures located in a position to assist the mixing process, the handling or automation of mixing vessel 12, a manufacturing process that uses mixing vessel 12, or the storage of mixing vessel 12.

Figure 2:
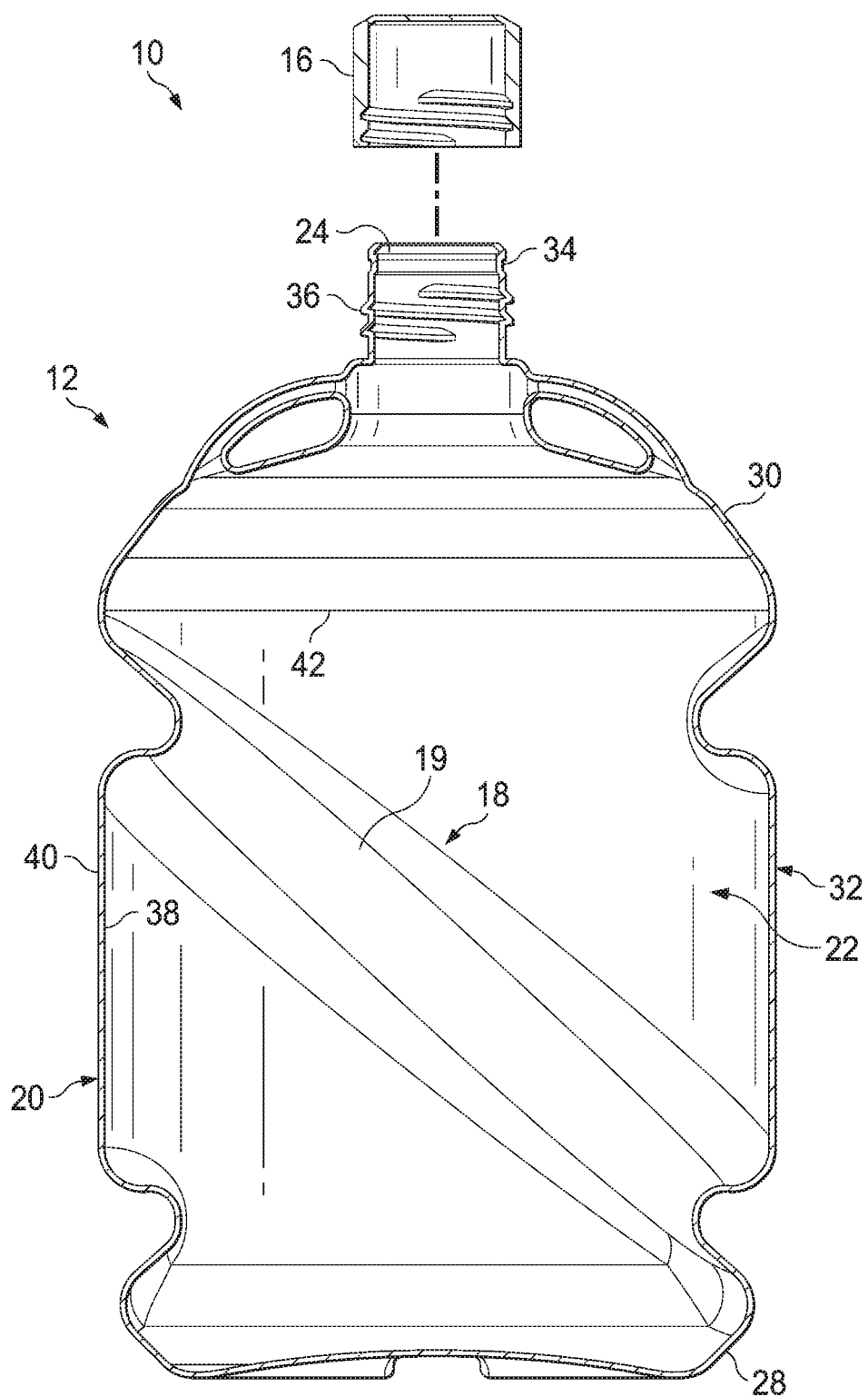
FIG. 2 illustrates an example cross-section of the mixing vessel of FIG. 1A, according to one or more embodiments.

Reaction chamber 22 is a void located in the interior cavity of mixing vessel 12. The peripheral boundary of reaction chamber 22 is formed by the interior facing sides 38 of outer housing 20 and raised surfaces 19 of internal mixing structure 18. FIG. 2 illustrates an example cross-section of mixing vessel 12 taken along axis 2-2 of FIG. 1A.

As shown therein, raised surfaces 19 penetrate reaction chamber 22, reducing its volume and resulting in a non-cylindrical shape. Accordingly, and as seen in FIGS. 1A, 1B and 2, reaction chamber 22 is generally non-cylindrical even though mixing vessel 12 is generally cylindrical.

Returning to FIGS. 1A and 1B with continuing reference to FIG. 2, opening 24 provides access to reaction chamber 22 and can be scaled to any suitable size relative to the volume and/or size of mixing vessel 12 or the intended biological production process. Opening 24 is configured to be sealed by any number of industry standard closures, such as closure 16. In one or more embodiments, opening 24 is designed for use with standard processing equipment used for sealing, siphoning, pouring, or otherwise accessing the interior of stock roller bottles or other bioreactors. For example, opening 24 may provide access to reaction chamber 22 to allow mixing vessel 12 to be used for sterile operations, gas infusion, degassing, mixing, circulation, and biological production. In one or more embodiments, opening 24 has approximately the same dimensions as a standard 50 liter roller bottle.

Figure 4A:
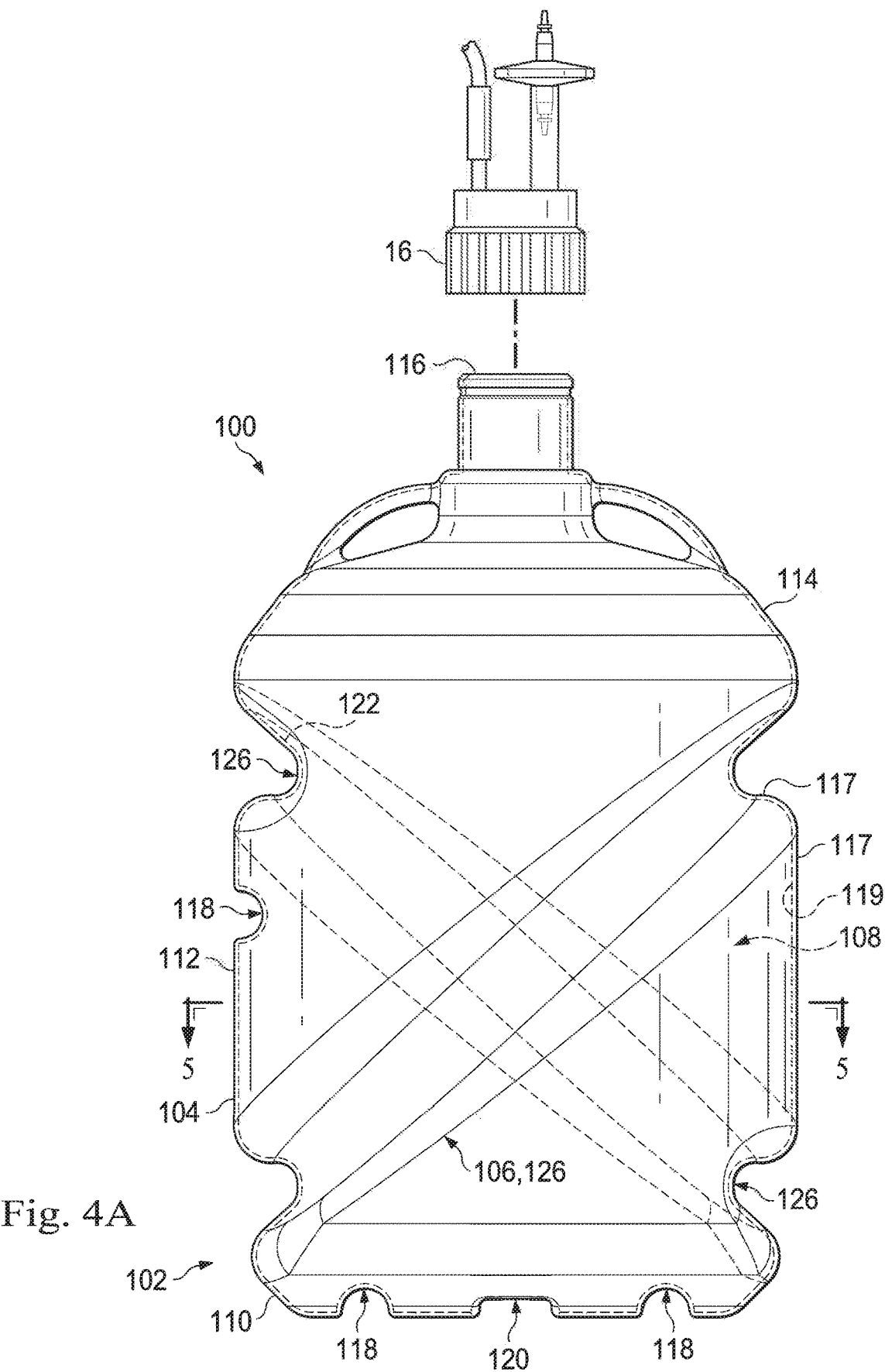
FIG. 4A illustrates an alternate example biological production system, according to one or more embodiments.
Figure 4B:
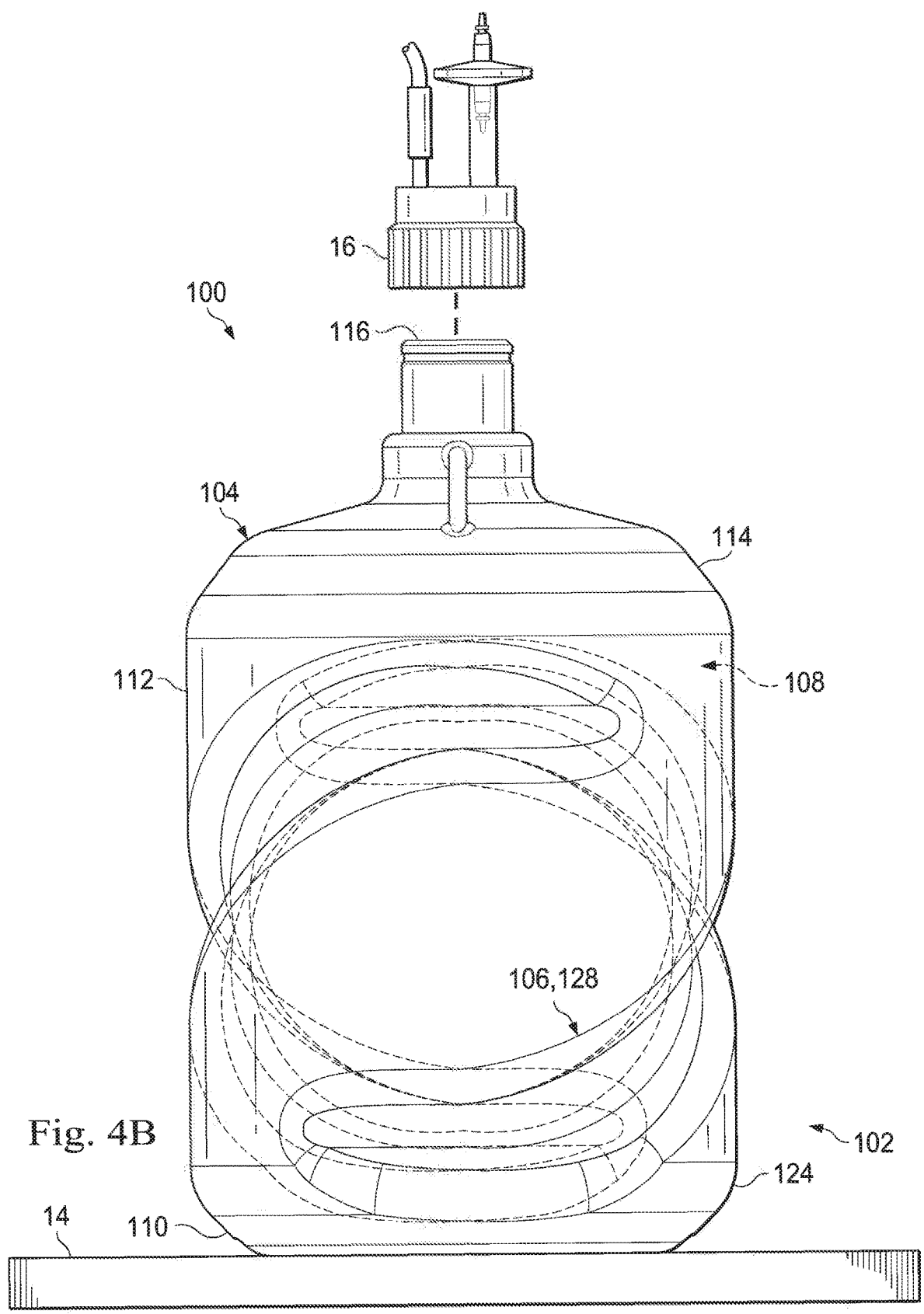
FIG. 4B illustrates an alternate example biological production system, according to one or more embodiments.

Closure 16 may be any apparatus or device that seals or limits access to reaction chamber 22 and/or mixing vessel 12. In one or more embodiments, closure 16 is standard processing equipment used for sealing, siphoning, pouring, or otherwise limiting access to the interior of stock roller bottles or other bioreactors. As seen in FIGS. 1A and 1B, in one or more embodiments, closure 16 is a threaded cap. As seen in FIGS. 4A and 4B, in one or more embodiments, closure 16 is a sanitary flange.

FIG. 3 illustrates mixing vessel 50, an alternate embodiment of mixing vessel 12 of FIGS. 1A and 1B. Mixing vessel 50 is a rigid, fixed-volume container operable for use as a bioreactor when sealed with a closure 16. Mixing vessel 50 includes internal mixing structure 52, outer housing 20, reaction chamber 54, and opening 24. Internal mixing structure 52 extends from, and is continuous with, outer housing 20 and together they define reaction chamber 54.

In one or more embodiments, internal mixing structure 52 includes two or more pitched blades each spaced approximately equidistant around the circumference of reaction chamber 54. For example, and as shown in FIG. 3, internal mixing structure 52 includes 3 pitched blades (e.g., blades 56 a-c, hereinafter "blades 56") each separated approximately 120 degrees apart. Blades 56 have interior facing sides 58 that create fluid movement within reaction chamber 54 when a rotational force is applied to mixing vessel 50.

Blades 56 may extend from the bottom end 28 to top edge 42 of the cylindrical wall 32 of mixing vessel 50. In such an embodiment, blades 56 have a height approximately equal to the height of cylindrical wall 32 of mixing vessel 50. As shown in FIG. 3, blades 56 may extend from the bottom end 28 beyond top edge 42 to top end 30 of mixing vessel 50. However, blades which run 100% of the height of mixing vessel 50 or 100% of the height of cylindrical wall 32 are not necessarily required. Blades 56 however, may be any suitable size as determined by the size of mixing vessel 50 and the desired flow parameters (e.g., laminar flow, turbulent mixing, and low shear mixing) within reaction chamber 54. In one or more embodiments, blades 56 do not extend from bottom end 28 to top edge 42. In one or more embodiments, blades 56 run from about 90% to about 10% of the height of the mixing vessel 50, from about 70% to about 30% of the height of the mixing vessel 50, or from about 55% to about 45% of the height of the mixing vessel 50. In one or more embodiments, mixing vessel 50 has dimensions similar to a standard 50 liter roller bottle and blades 56 have a height from about 10 centimeters (cm) to about 35 cm, which represents blades that run from about 50% to about 100% of the height of the 50 liter roller bottle.

Similarly, blades 56 may be centered as in FIG. 3, or may be preferentially oriented near top end 30 or bottom end 28 to produce desired mixing parameters. As used herein, blades 56 are said to begin "near" top end 30 and/or "near" top edge 42, if they begin a distance of less than 5% of the total height of cylindrical wall 32 from top edge 42. Similarly, as used herein, blades 56 are said to begin "near" bottom end 28 if they begin a distance of less than 5% of the total height of cylindrical wall 32 from bottom end 28. In one or more embodiments, blades 56 are formed near top end 30 and extend to approximately the midpoint of mixing vessel 50. In this exemplary embodiment, blades 56 would begin a distance of 5% or less from top end 30 and run approximately 50% of the height of cylindrical wall 32. In one or more embodiments, mixing vessel 50 has blades 56 that extend from bottom end 28 to the middle of the mixing vessel 50 (i.e. blades 56 that run 50% of the height of cylindrical wall 32). In this exemplary embodiment, fluid 26 includes a less disturbed layer near the surface and a well-mixed layer below the surface. Non-uniform mixing may be beneficial in certain cell growth environments and/or may allow for certain components (e.g., reaction by-products) to be decanted if necessary.

Reaction chamber 54 is a void located in the interior cavity of mixing vessel 50. The peripheral boundary of reaction chamber 54 is formed by the interior facing sides 38 of outer housing 20 and interior facing sides 58 of blades 56 of internal mixing structure 52. Interior facing sides 58 of blades 56 penetrate reaction chamber 54, reducing its volume and resulting in a non-cylindrical shape. Accordingly, and as seen in FIG. 3, reaction chamber 54 is generally non-cylindrical even though mixing vessel 50 is generally cylindrical.

In one or more embodiments, mixing vessel 12 and/or mixing vessel 50 is a cylindrical reactor, a roller bottle, or any other rigid vessel capable of being mass produced from material suitable for aseptic processing. As shown in FIGS. 1A, 1B, 3, 4A and 4B, in one or more embodiments, mixing vessels 12 and 50 are substantially cylindrical and have a diameter to height ratio of approximately 1:2. In one or more embodiments, mixing vessels 12 and/or 50 can be scaled to accommodate biological processing ranging from small scale laboratory processes with volumes from about 1 liter to about 20 liters to large scale production processes with volumes from about 20 liters to about 1000 liters. In one or more embodiments, mixing vessel 12 and/or mixing vessel 50 is sized according to one of the following embodiments: 1 liter, 10 liters, 20 liters, 50 liters, 100 liters, 200 liters, and 1000 liters.

In one or more embodiments, mixing vessels 12 and 50 are designed for use with standard processing equipment for handling and transporting roller bottles or other bioreactors. In one or more embodiments, mixing vessels 12 and 50 are designed for use with standard agitation devices well known to those of ordinary skill in the art such as roller tables, shaker tables, and rocking tables that provide horizontal, vertical, inversion, oscillation, or other rotational forces. In one or embodiments, agitation device 14 is any machine capable of providing a force (e.g., shaking, oscillation, inversion, horizontal and/or vertical rotational force) of sufficient amplitude, frequency and duration to create an oscillatory agitation of the materials contained within reaction chambers 22 and/or 54. Accordingly, while mixing vessels 12 and 50 can be scaled to any suitable size, in one or more embodiments, vessels 12 and 50 approximate the standard shape, size, and dimensions of stock roller bottles. Similarly, in one or more embodiments, mixing vessels 12 and 50 approximate the standard shape, size, and dimensions of stock roller bottles but only to the extent necessary to allow mixing vessels 12 and 50 to be compatible with standard equipment used in the industry. For example, in one or more embodiments, mixing vessel 12 and/or mixing vessel 50 have approximately the same diameter and height dimensions as a standard 50 liter roller bottle.

In operation, materials (e.g., reactants) are transferred into the mixing vessel (e.g., mixing vessel 12, mixing vessel 50) through opening 24 and then the mixing vessel is sealed. The mixing vessel is loaded onto an agitation device 14 which provides a force of sufficient amplitude, frequency and duration to create an oscillatory agitation of fluid 26 contained within the reaction chambers 22 and/or 54. In one or more embodiments, the agitation device 14 is configured to rotate the mixing vessel 12, 50 at a rate of 10-100 rpm, 10-60 rpm, 15-55 rpm, 20-50 rpm, 25-40 rpm, or 20-40 rpm. In one or more embodiments, raised surfaces 19, blades 56 and/or internal mixing structure 18, push fluid 26 to create dispersion in the chamber. Without being limited by theory, the large area of raised surfaces 19 and/or blades 56 allow a large energy transfer from mixing vessels 12 and 50, respectively, to fluid 26, causing laminar or turbulent motion of fluid 26. Mixing parameters such as 1) mixing time, 2) magnitude of force applied by agitation device 14, and 3) number of agitation cycle(s) are determined by the product requirements, specifically whether turbulent or laminar mixing is required and whether the reaction chamber is a high shear or low shear environment. For processes that involve biological production, the aforementioned mixing parameters are often dependent upon the biological process of the cells.

For example, mixing vessel 12 is fitted with closure 16 and then loaded on a turntable (vertical) or a roller mill (horizontal) and agitated for 12 hours at 28 revolutions per minute (rpm). During the agitation cycle, internal mixing structure 18 facilitates low-shear agitation of fluid 26 by accelerating fluid 26 as it passes over internal mixing structure 18 and/or raised surfaces 19 causing a change in direction and facilitating a homogenous solution. Upon completion of the desired processing cycle(s), mixing vessel 12 is removed from the agitation device 14.

As another example, mixing vessel 50 is fitted with a screw cap and then loaded on a shaker table and agitated for 36 hours at 120 hertz. During the agitation cycle, internal mixing structure 52 facilitates low-shear agitation of fluid 26 by accelerating fluid 26 as it passes over interior facing sides 58 of blades 56. Upon completion of the desired processing cycle(s), mixing vessel 50 is removed from the agitation device 14 and fluid 26 is evacuated by pouring.

In one or more embodiments, fluid 26 (e.g., reaction products, byproducts, unused reactants) are evacuated by siphoning, pumping, or pouring. In one or more embodiments, fluid 26 may remain in mixing vessels 12 and 50 and be stored therein. In one or more embodiments, fluid 26 may remain in mixing vessels 12 and 50 and be re-agitated at a later time. In one or more embodiments, additional agitation cycles are completed after reactants are added to or reaction products and/or byproducts are removed from reaction chambers 22 or 54 through opening 24.

FIGS. 4A and 4B illustrate system 100 for biological production. As shown in FIGS. 4A and 4B, system 100 includes mixing vessel 102 which includes outer housing 104 and mixing curve 106. System 100 may optionally include a closure 16 such as the sanitary flange shown in FIGS. 4A and 4B and/or the threaded cap of FIGS. 1A and 1B. System 100 may also include an agitation device, such as agitation device 14 of FIGS. 1A and 1B.

Mixing vessel 102 is a rigid, fixed-volume container operable for use as a bioreactor when sealed. In one or more embodiments, mixing vessel 102 is a cylindrical reactor, a roller bottle, or any other rigid vessel capable of being mass produced from material suitable for aseptic processing. As shown in FIGS. 4A and 4B, in one or more embodiments, mixing vessel 102 is substantially cylindrical and has a diameter to height ratio of approximately 1:2. In one or more embodiments, mixing vessel 102 can be scaled to accommodate biological processing ranging from small scale laboratory processes with volumes from about 1 liter to about 10 liters to large scale production processes with volumes from about 20 liters to about 1000 liters. In one or more embodiments, mixing vessel 102 is sized according to one of the following embodiments: 1 liter, 10 liters, 20 liters, 50 liters, 100 liters, 200 liters, and 1000 liters.

In one or more embodiments, mixing vessel 102 is designed for use with standard processing equipment for handling and transporting roller bottles or other bioreactors such as those described with respect to system 10 of FIGS. 1A and 1B. While mixing vessel 102 can be scaled to any suitable size, in one or more embodiments, mixing vessel 102 approximates the standard shape, size, and dimensions of stock roller bottles. Similarly, in one or more embodiments, mixing vessel 102 approximates the standard shape, size, and dimensions of stock roller bottles but only to the extent necessary to allow mixing vessel 102 to be compatible with standard equipment used in the industry. For example, in one or more embodiments, mixing vessel 102 has approximately the same diameter and height dimensions as a standard 50 liter roller bottle.

Figure 5:
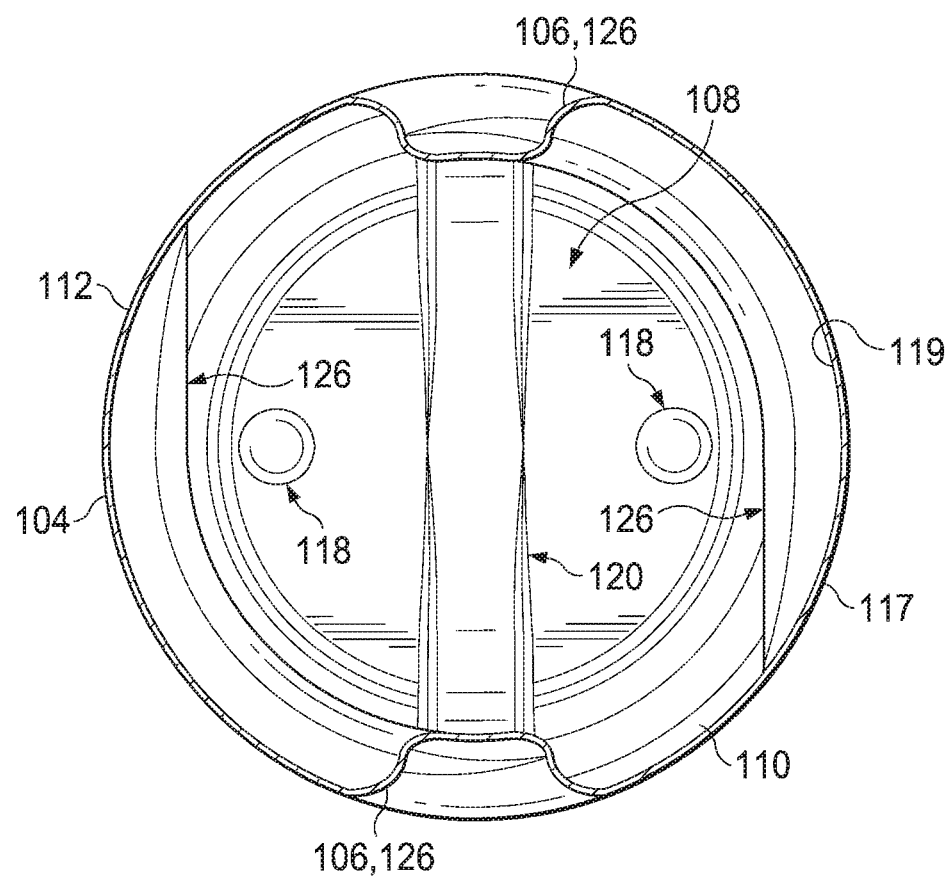
FIG. 5 illustrates an example cross-section of the mixing vessel of FIG. 4A, according to one or more embodiments.

FIG. 5 illustrates an example cross-section of mixing vessel 102 taken along axis 5-5 of FIG. 4A.

As seen in FIGS. 4A and 5, outer housing 104 is a continuous, rigid shell that forms the outer confines of mixing vessel 102 and interior cavity 108. In one or more embodiments, outer housing 104 has interior facing and exterior facing sides, 119 and 117, respectively. In some embodiments, outer housing 104 retains a generally uniform thickness. In one or more embodiments, outer housing 104 has a thickness that ranges from about 2 mm to about 12 mm, from about 4 mm to about 10 mm, or from about 6 mm to about 8 mm. Outer housing 104 extends from a closed bottom end 110 along cylindrical wall 112 to an opposing top end 114 and concludes at opening 116. Opening 116 provides access to interior cavity 108 and can be scaled to any suitable size relative to the volume and/or size of mixing vessel 102 or the intended biological production process. Opening 116 is configured to be sealed by any number of industry standard closures, such as closure 16 of system 10. In one or more embodiments, opening 116 is designed for use with standard processing equipment used for sealing, siphoning, pouring, or otherwise accessing the interior of stock roller bottles or other bioreactors.

Mixing curve 106 extends from the interior side 119 of outer housing 104. In some embodiments, outer housing 104 generally follows the contours of mixing curve 106. Accordingly, unlike the exterior facing side 40 of outer housing 20 of FIGS. 1A and 1B which retains a substantially cylindrical exterior facing side, in one or more embodiments, the exterior side 117 of outer housing 104 is generally non-cylindrical and includes one or more indentations (e.g., structures 118, notch 120) where the shape of outer housing 104 departs from a cylindrical profile. In one or more embodiments, raised surface 122 may also cause the shape of outer housing 104 to depart from a purely cylindrical profile. Similarly, the interior side 119 of outer housing 104 is generally non-cylindrical and includes one or more indentations (e.g., structures 118, notch 120) or raised surfaces (raised surface 122) where the shape of outer housing 104 departs from a substantially cylindrical profile. Outer housing 104 forms the peripheral boundary of interior cavity 108. Accordingly, interior cavity 108 is also generally non-cylindrical.

Outer housing 104 may be molded, cast, extruded, pultruded, or fabricated to minimize cost. In one or more embodiments, outer housing 104 is a continuous, uniform body formed from a single unitary material. In one or more embodiments, outer housing 104 is seamless or substantially seamless. For example, and as shown in FIG. 4B, cylindrical wall 112 and bottom end 110 may meet in a chamfered corner 124. However, in one or more embodiments, outer housing 104 may include one or more seams, areas of overlap, connection points, non-uniformities, or other byproducts of the manufacturing process as described with respect to top edge 42 of FIG. 1A and FIG. 3.

In one or more embodiments, bottom end 110, cylindrical wall 112, and/or outer housing 104 may comprise one or more notches, indentations, dimples, divots, or structures 118 added to create turbulence and/or disrupt any solids or dense material that may collect on the bottom of mixing vessel 102. Structures 118 may have the same or varying sizes, shapes, and dimensions. Structures 118 may be uniformly or randomly distributed. Unlike top edge 42 of FIGS. 1A and 1B which is a byproduct from the manufacture of the mixing vessel 12, structures 118 are added to create turbulence and/or disrupt any solids or dense material that may collect on the bottom of mixing vessel 102. In one or more embodiments, structures 118 are small half-spheres that extend into the interior of mixing vessel 102. The size, number, and arrangement of the half-spheres depend upon the size of the vessel. In one or more embodiments, the diameters of the half-spheres are from about 4 mm to about 100 mm, from about 6 mm to about 25 mm, or from about 10 mm to about 14 mm depending upon the size of the vessel. In one or more embodiments, structures 118 are hemicylindrical or hemispherical having diameters, based on the volume of the mixing vessel, of 0.05-2 mm/L, 0.15-1.75 mm/L, 0.25-1.5 mm/L, 0.5-1.25 mm/L, or 0.75-1 mm/L.

In one or more embodiments, bottom end 110, cylindrical wall 112, and/or outer housing 104 may comprise one or more notches, indentations, dimples, trenches, or internal structures located in a position to assist with the handling or automation of mixing vessel 102, a manufacturing process that uses mixing vessel 102, or the storage of mixing vessel 102. For example, in some embodiments, notch 120 assists the loading or unloading of mixing vessel 102 to and from an agitation device, such as agitation device 14 described in more detail with reference to system 10 of FIGS. 1A and 1B. In one or more embodiments, notch 120 is located so that mixing vessel 102 is more easily secured to machinery. In one or more embodiments, notch 120 approximates an elongated trench and is located on the bottom end 110 of the mixing vessel 102 so that mixing vessel 102 is more easily stacked for storage. For example, notch 120 is positioned so that closure 16 aligns with notch 120 when two or more mixing vessels 102 are stacked on top of each other.

Structures 118 and notch 120 may have the same or different dimensions, shapes, and sizes compared to each other, however structures 118 and notch 120 will generally have a combined area that is at least 10 times smaller than mixing curve 106. Nevertheless, like mixing curve 106, structures 118 and notch 120 extend from and are fabricated concurrently with outer housing 104 from a single unitary material. As described with respect to outer housing 20 of system 10, in one or more embodiments, outer housing 104 may be made of any material or combination of materials that are compatible with the expected product mixture and processing requirements.

In some embodiments, mixing curve 106 is a generally c-shaped mixing curve, such as mixing curves 126 and 128 illustrated in FIG. 4A and FIG. 4B, respectively. Each of mixing curves 126 and 128 is a smooth three-dimensional curve that passes over the entire circumference of mixing vessel 102 one or more times as it travels from the bottom end 110 to the top end 114 of the mixing vessel 102. As illustrated in FIG. 4A, the entire length of exterior side 117 of mixing curve 126 departs from the cylindrical nature of mixing vessel 102 such that interior side 119 of mixing curve 126 penetrates the interior cavity 108 of mixing vessel 102. In some embodiments, in order to maintain a low shear environment within interior cavity 108, the interior sides of mixing curves 126 and 128 have a rounded profile with no sharp edges. In one or more embodiments, mixing vessel 102 is a 50 liter vessel and mixing curves 126 and 128 have about a 0.5 inch radius that traverses horizontally along the circumference of mixing vessel 102 (a zero degree pitch) for a length from about 0 mm to about 375 mm and then traverses toward top end 114 along the side of the mixing vessel 102 at an angle of from about 15 degrees to about 70 degrees relative to the bottom end 110 (15 degree pitch and 70 degree pitch, respectively). As mixing curves 126 and 128 near top end 114, they taper back to a zero degree pitch for a length from about 0 mm to about 375 mm.

In one or more embodiments, mixing curve 126 is a smooth three-dimensional mixing curve that traverses the circumference of mixing vessel 102 as it travels from the bottom end 110 to the top end 114 of mixing vessel 102 or a continuous double helix-like structure that extends from the bottom end 110 to the top end 114 of mixing vessel 102 as described with respect to internal mixing structure 18 of mixing vessel 12 of system 10. In one or more embodiments, mixing curve 126 is a smooth three-dimensional mixing curve that traverses a portion of the circumference of mixing vessel 102 as it travels less than 100% of the length of mixing vessel 102 as described with respect to internal mixing structure 18 of mixing vessel 12 of system 10. In one or more embodiments, mixing curve 106 includes two or more pitched blades (e.g., blades 56) as described with respect to internal mixing structure 52 of mixing vessel 50. Similarly, mixing curves 126 and 128 may be used with mixing vessel 12 and/or mixing vessel 50.

In operation, materials (e.g., reactants) are transferred into a mixing vessel 102 through opening 116 and sealed (e.g., with closure 16). Mixing vessel 102 is loaded onto an agitation device 14 which provides a force of sufficient amplitude, frequency and duration to create an oscillatory agitation of fluid 26 contained within interior cavity 108. During the agitation cycle, mixing curve 106 facilitates low-shear agitation of fluid 26 by accelerating fluid 26 as it passes over the interior surfaces of mixing curves 126 and/or 128. The mixing curves 126 and/or 128 push the fluid 26 to create dispersion in the chamber. Without being limited by theory, the large area of the mixing curves 126 and/or 128 allow a large energy transfer from mixing vessel 102 to fluid 26 causing laminar or turbulent motion of fluid 26. The time of mixing, magnitude of force applied by agitation device 14, whether the environment within mixing vessel 102 and/or interior cavity 108 is high or low shear, and/or the amount of energy transferred from mixing curves 126 and 128 are determined by the product requirements. For biological processes, the aforementioned mixing parameters are often dependent upon the biological process of the cells. Upon completion of the desired processing cycle(s), mixing vessel 102 is removed from the agitation device 14. In one or more embodiments, fluid 26 is evacuated by siphoning, pumping, or pouring, remains in mixing vessel 102 for storage, or remains in mixing vessel 102 and is re-agitated at a later time. In one or more embodiments, mixing vessel 102 may be used to create a mixture, promulgate cells, or harvest cellular by-products.

As use herein, the term "or" is inclusive and not exclusive, unless expressly indicated otherwise or indicated otherwise by context. Therefore, herein, "A or B" means "A, B, or both," unless expressly indicated otherwise or indicated otherwise by context. Moreover, "and" is both joint and several, unless expressly indicated otherwise or indicated otherwise by context. Therefore, herein, "A and B" means "A and B, jointly or severally," unless expressly indicated otherwise or indicated otherwise by context.

The scope of this disclosure encompasses all changes, substitutions, variations, alterations, and modifications to the example embodiments described or illustrated herein that a person of ordinary skill in the art would comprehend. The scope of this disclosure is not limited to the example embodiments described or illustrated herein. Moreover, although this disclosure describes and illustrates respective embodiments herein as including particular components, elements, functions, operations, or steps, any of these embodiments may include any combination or permutation of any of the components, elements, functions, operations, or steps described or illustrated anywhere herein that a person of ordinary skill in the art would comprehend. Furthermore, reference in the appended claims to an apparatus or system or a component of an apparatus or system being adapted to, arranged to, capable of, configured to, enabled to, operable to, or operative to perform a particular function encompasses that apparatus, system, component, whether or not it or that particular function is activated, turned on, or unlocked, as long as that apparatus, system, or component is so adapted, arranged, capable, configured, enabled, operable, or operative.

EXAMPLES

A bioreactor according to the present disclosure and a traditional prop mixer were tested side by side to compare dissolution rates. Three different types of bovine serum albumin (BSA) were utilized for different solubility characteristics. Namely, lipid modified albumin A, standard grade albumin B, and fatty acid-free albumin C were each separately dissolved in water (5 wt % of albumin) at room temperature.

The prop mixer was operated at 90 rpm. The bioreactor was rotated on a turntable at 30 rpm. Each dissolution was repeated three times; averages and standard deviations are summarized in the table below.

|  | Bioreactor | | Prop Mixer | |
| --- | --- | --- | --- | --- |
|  | Time (min) | σ | Time (min) | σ |
| Albumin A | 35.7 | 1.4 | 43.0 | 1.4 |
| Albumin B | 47.0 | 1.4 | 52.3 | 0.7 |
| Albumin C | 61.3 | 2.8 | 72.3 | 2.8 |

As shown in the table above, the bioreactor was more efficient in the dissolution of a 5% BSA solution in water as compared with a traditional prop mixer. In addition, the bioreactor had minimal to no foaming, whereas the prop mixer demonstrated slight foaming.

What is claimed is:

1. A mixing vessel, comprising:
   a rigid outer housing formed of a single unitary material and comprising a closed bottom end, a top end opposite the bottom end including a neck defining an opening configured to be sealed with a closure, and a cylindrical wall integrally formed with, and extending between, the bottom end and the top end, the rigid outer housing tapering from the cylindrical wall to the neck such that a diameter of the cylindrical wall is greater than a diameter of the neck;
   a reaction chamber within the housing; and
   an internal mixing structure comprising at least two raised surfaces integrally formed with, and extending from, the cylindrical wall into the reaction chamber;
   wherein each of the at least two raised surfaces extends from 90 degrees to 270 degrees around a circumference of the cylindrical wall;
   wherein the internal mixing structure completely traverses the circumference of the cylindrical wall between the bottom end and the top end; and
   wherein the mixing vessel is configured to provide low shear agitation to materials contained within the reaction chamber in response to an externally applied force.

2. The mixing vessel according to claim 1, comprising three raised surfaces positioned equidistant around a circumference of the cylindrical wall.

3. The mixing vessel according to claim 2, wherein the raised surfaces each have a pitch angle of between 15 degrees and 70 degrees relative to the bottom end.

4. The mixing vessel according to claim 1, wherein each of the at least two raised surfaces extends from the cylindrical wall between 0.25 mm to 2 mm per liter of total volume of the mixing vessel.

5. The mixing vessel according to claim 1,
   wherein a height of the cylindrical wall measured from the bottom end to the top end is constant around a circumference of the cylindrical wall; and
   wherein the at least two raised surfaces extend along 50% to 100% of the height of the cylindrical wall.

6. The mixing vessel according to claim 1, wherein the housing has an average thickness of 0.01 mm to 0.30 mm per liter of total volume of the mixing vessel.

7. The mixing vessel according to claim 1, further comprising one or more structures extending from the bottom end into the reaction chamber.

8. The mixing vessel according to claim 7, wherein the structures are hemicylindrical or hemispherical and have a diameter of from 0.05 mm to 2 mm per liter of total volume of the mixing vessel.

9. The mixing vessel according to claim 1,
wherein each of the at least two raised surfaces extends from 180 degrees to 270 degrees.

10. The mixing vessel according to claim 1,
wherein an exterior surface of the cylindrical wall has an undulation at the location of each of the at least two raised surfaces of the internal mixing structure.

11. The mixing vessel according to claim 1,
wherein the surface area of the at least two raised surfaces is from 20 percent to 60 percent of the surface area of the cylindrical wall.

12. The mixing vessel according to claim 1, further comprising cells in a liquid medium located within the reaction chamber.

13. The mixing vessel according to claim 1,
wherein the at least two raised surfaces comprises a first raised surface and a second raised surface;
wherein each of the first and second raised surfaces comprises axially spaced apart first and second ends; and
wherein the first and second raised surfaces, collectively, completely traverse the circumference of the cylindrical wall between the bottom end and the top end.

14. A biological production system, comprising:
a mixing vessel comprising:
  a rigid outer housing comprising a closed bottom end, a top end opposite the bottom end including a neck defining an opening, and a cylindrical wall integrally formed with, and extending between, the bottom end and the top end, the rigid outer housing tapering from the cylindrical wall to the neck such that a diameter of the cylindrical wall is greater than a diameter of the neck;
  a reaction chamber within the housing; and
  an internal mixing structure comprising at least two raised surfaces integrally formed with, and extending from, the cylindrical wall into the reaction chamber;
  wherein each of the at least two raised surfaces extend from 90 degrees to 270 degrees around a circumference of the cylindrical wall;
  wherein the internal mixing structure completely traverses the circumference of the cylindrical wall between the bottom end and the top end; and
  wherein the outer housing and the internal mixing structure are formed of a single unitary material;
a closure configured to seal the opening; and
an agitation device;
wherein the mixing vessel is configured to provide low shear agitation to materials contained within the reaction chamber in response to an externally applied force from the agitation device.

15. The system according to claim 14, wherein the agitation device is a turntable.

16. The system according to claim 14, wherein the mixing vessel has a total volume of 1 liter to 20 liters.

17. The system according to claim 14, wherein the mixing vessel has a total volume of 20 liters to 1000 liters.

18. The system according to claim 14, wherein the mixing vessel further comprises cells in a liquid medium located within the reaction chamber.

19. The mixing vessel according to claim 14,
wherein the at least two raised surfaces comprises a first raised surface and a second raised surface;
wherein each of the first and second raised surfaces comprises axially spaced apart first and second ends; and
wherein the first and second raised surfaces, collectively, completely traverse the circumference of the cylindrical wall between the bottom end and the top end.

20. A method of mixing cells, the method comprising:
providing a mixing vessel comprising:
  a rigid outer housing comprising a closed bottom end, a top end opposite the bottom end including a neck defining an opening, and a cylindrical wall integrally formed with, and extending between, the bottom end and the top end, the rigid outer housing tapering from the cylindrical wall to the neck such that a diameter of the cylindrical wall is greater than a diameter of the neck;
  a reaction chamber within the housing; and
  an internal mixing structure comprising at least two raised surfaces integrally formed with, and extending from, the cylindrical wall into the reaction chamber;
  wherein each of the at least two raised surfaces extend from 90 degrees to 270 degrees around a circumference of the cylindrical wall;
  wherein the internal mixing structure completely traverses the circumference of the cylindrical wall between the bottom end and the top end; and
  wherein the outer housing and the internal mixing structure are formed of a single unitary material;
depositing cells in a liquid medium into the reaction chamber; and
agitating the mixing vessel using an agitation device.

21. The method according to claim 20, wherein the agitation device is a turntable and the agitating comprises rotating the mixing vessel at a rate of 10 rpm to 60 rpm.

22. The method according to claim 20, comprising three raised surfaces positioned equidistant around a circumference of the cylindrical wall.

23. The method according to claim 20, wherein the mixing vessel has a total volume of 1 liter to 20 liters.

24. The system according to claim 20, wherein the mixing vessel has a total volume of 20 liters to 1000 liters.

* * * * *